United States Patent [19]

Binder et al.

[11] Patent Number: 5,303,598
[45] Date of Patent: Apr. 19, 1994

[54] PROCESS AND APPARATUS FOR TAKING A REPRESENTATIVE MILK SAMPLE

[75] Inventors: Wilhelm Binder, Tiefenbach; Gerhard Raudszus, Zachenberg, both of Fed. Rep. of Germany

[73] Assignee: Ultrakust Electronic GmbH, Gotteszell, Fed. Rep. of Germany

[21] Appl. No.: 711,535

[22] Filed: Jun. 10, 1991

[30] Foreign Application Priority Data

Jun. 8, 1990 [DE] Fed. Rep. of Germany ....... 4018468

[51] Int. Cl.⁵ .............................................. G01N 1/14
[52] U.S. Cl. .............................. 73/863.01; 73/863.02; 73/864.34; 364/509
[58] Field of Search .......... 73/863.01, 863.02, 863.03, 73/864.34, 864.35, 863.83, 863.84; 364/509

[56] References Cited

U.S. PATENT DOCUMENTS

| | | | |
|---|---|---|---|
| 3,751,983 | 8/1973 | Kradel et al. | 73/863.01 |
| 4,149,411 | 4/1979 | Fisher et al. | 73/198 |
| 4,165,033 | 8/1979 | Nielson et al. | 235/439 |
| 4,333,356 | 6/1982 | Bartels et al. | 73/864.34 X |
| 4,367,043 | 1/1983 | Sweet et al. | 340/712 X |
| 4,455,483 | 6/1984 | Schönhuber | 364/403 X |
| 4,484,593 | 11/1984 | Russell | 73/863.01 |
| 4,660,607 | 4/1987 | Griffith et al. | 364/510 X |
| 4,798,095 | 1/1989 | Itoh | 73/863.01 |
| 4,803,887 | 2/1989 | Senden et al. | 73/864.34 X |
| 5,051,920 | 9/1991 | Reams et al. | 364/509 |

Primary Examiner—Tom Noland
Attorney, Agent, or Firm—Keck, Mahin & Cate

[57] ABSTRACT

A process and apparatus are disclosed for taking a representative milk sample during the delivery of a milk charge from one container to another. With respect to the errors encountered in operating peristaltic pumps with different speeds of revolution, the invention predetermines a corrected pumping characteristic as a function of an acceptance characteristic and correspondingly controls the taking of samples.

13 Claims, 2 Drawing Sheets

PROCESS AND APPARATUS FOR TAKING A REPRESENTATIVE MILK SAMPLE

BACKGROUND OF THE INVENTION

The invention relates to a process for taking a representative milk sample and to an apparatus, particularly for performing the process.

A process and an apparatus of the aforementioned type are e.g. known from DE 35 02 858 A1. In the known apparatus a milk sample is actively pumped by means of a peristaltic pump from a delivery line into a sample bottle for example during the transfer of a milk charge from one container to another. The peristaltic pump is controlled in such a way that, in accordance with a previously inputted desired quantity for the milk charge, the sample bottle for the latter is filled in accordance with a desired volume.

In order to obtain a reproducible desired volume, it is necessary to have information on the acceptance capacity of the milk collecting container which may be a truck or trucks. For this purpose hitherto one parameter has been fixedly predetermined in a preprogrammed manner, so that the sample bottle for receiving the milk sample has been constantly filled to a greater or lesser extent.

As the aim is to take a continuous representative milk sample of the entire milk charge, the milk sample removal process must be controllable as a function of the total milk charge volume. The term a representative milk sample is understood to mean that only a maximum volume is available in the sample bottle intended for the milk sample and on the other hand that, if possible, the milk sample should have a roughly constant volume, independently of whether a lower volume milk charge or a very large milk charge is delivered. The sought constant volume for the milk sample results from the fact that certain minimum milk sample quantities are required for investigations and tests.

Another objective of the representative milk sample is to draw the latter over the entire delivery cycle of the corresponding milk charge. However, since, as a function of the volume, the milk charges are sucked with different deliveries, e.g. from a tank and pumped into the milk collecting truck or tanker, so that different delivery times occur, account must also be taken of this aspect within the scope of a representative milk sample.

In addition, when using a peristaltic pump for taking a representative milk sample, a further problem occurs in that the delivered volume is not in a linear relationship with the speed of revolution of the peristaltic pump. If it is assumed, for example, that a peristaltic pump delivers a volume z1 after y revolutions in the case of a speed of revolution of x1, then normally the volume z2 delivered at a higher speed x2 after y revolutions will be smaller than z1. This is attributed to the fact that the hose or tube used does not have sufficient time, particularly if high speeds are used, to reassume its original hose or tube diameter, in order to achieve its normal capacity.

Thus, with a larger volume of a milk charge to be delivered, its delivery takes longer, the milk sample being taken in a continuous manner and as a result of the lower speed of revolution of the peristaltic pump a higher than desired milk sample volume is taken.

Further problems in the delivery of a milk charge and taking a representative milk sample are that the delivery or pumping capacity characteristic may be influenced by factors which lead to a divergence compared with the desired or nominal delivery. Reference is e.g. made to different or too narrow cross-sections in the delivery line or in the collecting area on the milk tank. The pumping capacity can also be influenced by filter fluff in the screen of the collecting line and possibly as a result of the drive this does not coincide with the nominal capacity or delivery. The way in which the milk is collected also affects the pumping capacity, if e.g. with a relatively large air admixture, particularly at the end of the delivery operation, milk is sucked from the tank or tanks, which are subject to a downward suction action, and which can be difficult to empty due to an inadequate installation of the tank. Problems can also occur due to incorrect handling by the driver during the delivery process.

Such fault and error sources consequently influence the delivery and delivery time for transferring a milk charge from one tank into another.

SUMMARY OF THE INVENTION

An object of the invention is to so improve a process and an apparatus of the aforementioned type, that the aforementioned disadvantages are minimized and with the aid of the control means for the pump, specifically a peristaltic pump, it is possible to take a representative milk sample, even for different milk charge volumes.

The invention takes account of an acceptance or collecting characteristic for the feed pump used for delivering the milk charge or for pumping round or recycling, as well as a pumping characteristic for the peristaltic pump. As a result of this pumping characteristic quantity losses at higher speeds of revolution can be compensated by a corresponding increase in the number of revolutions n. On controlling the sampling means having the peristaltic pump by such means there is a correction to the speed of revolution of the peristaltic pump in accordance with the stored pump characteristic.

In addition, according to the invention, the delivery for the recycling of a milk charge is controlled as a function of an acceptance or collecting characteristic. In order to ensure an effective recycling or delivery of a corresponding milk charge, modern milk collecting trucks operate as a function of the volume of the milk charge to be recycled with different delivery rates. Thus, the apparatus for delivering the milk charge in the case of a milk collecting truck or tanker up to the collection of 40 liters (l) can be operated at an average delivery of 230 l/min, whereas e.g. 100 l can be recycled with a delivery of 260 l/min and delivery up to e.g. 320 l/min and higher are possible.

Thus, the delivery influences the control of the peristaltic pump, because for this there must not only be a time, but also a volume dependence. Thus, the plotting of the collecting characteristic is empirically determined by different quantities and is also stored. This storage appropriately takes place in the form of supporting values (interpolation nodes) for different quantities, e.g. at a milk charge up to 10 l with a delivery of 150 l/min or at a milk charge up to 40 l with a delivery of 230 l/min. As a function of the number of such supporting values, it is possible to very accurately simulate the collecting characteristic.

Appropriately the maximum possible sample bottle volume, into which is passed the representative milk sample is defined with a degree of overfilling of e.g.

120%. In other words the sample bottle is normally filled to a significant extent, e.g. up to 70% of its actual volume in the case of coincidence between the desired and actual volumes of the milk charge to be delivered. With an increased actual milk charge volume, the possibility then exists to take a further milk sample for the milk charge volume exceeding the desired volume up to a predeterminable and programmable degree of overfilling, so that reference can genuinely be made to a representative milk sample.

The taking of the milk sample is appropriately controlled via sensors, which determine the start and finish of milk charge delivery.

To ensure an effective pumping round or recycling of the milk charge, advantageously working takes places with stepped deliveries. In cases where the predetermined degree of overfilling of the sample bottle is not sufficient and further milk charge delivery takes place, the milk sample taken can no longer be looked upon as representative, so that an error code is established.

In order to be able to determine and eliminate practice-related error sources, e.g. different diameters for the delivery hoses, etc., from a process and apparatus standpoint, the desired delivery time is predetermined and compared with the actual delivery time. If the desired delivery time is exceeded, an error code is outputted, taking account of the actual milk charge volume.

The apparatus according to the invention comprises at least one data acquisition unit, which is connected to a control mechanism. The function of the latter is to control the sampling means and in particular the peristaltic pump as a function of the pumping of the pumping and collecting characteristic and while taking account of the determined desired and actual data.

The storage of both characteristics appropriately takes place in the control mechanism, but for special purposes advantages also result from a decentral storage in the sampling means or the data detection unit.

With the aid of the inventive process and the corresponding apparatus it is consequently possible to obtain a representative milk sample, making it possible not only to eliminate volume losses due to the hitherto known control means for peristaltic pumps, but also the error factors which occur in practice. In addition, the process and apparatus also have the flexibility for defining and storing degrees of overfilling for the sample bottle, so that apart from extreme divergences, it is also possible to determine with a representative milk sample larger milk charge volumes, which significantly exceed the desired values.

The invention is described in greater detail hereinafter relative to a block circuit diagram and two characteristics.

DESCRIPTION OF THE PREFERRED EMBODIMENT(S)

Figure 1:
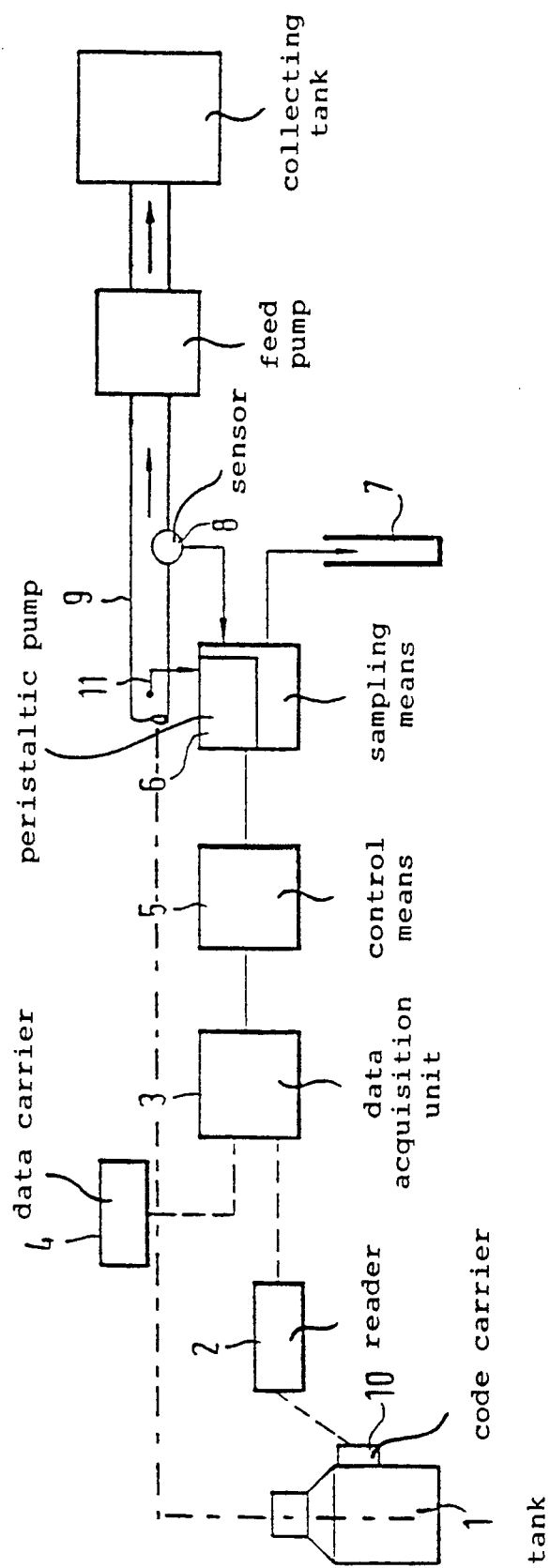
FIG 1 is a block circuit diagram of an apparatus according to the invention.

FIG. 1 diagrammatically shows a block circuit diagram of an apparatus for taking a representative milk sample during the delivery of a milk charge from one tank to another. The milk charge to be delivered is contained in a tank 1, which e.g. has on its outside a code carrier 10 for identifying the supplier. By means of a reader 2 the said code carrier is read and the data inputted into a data acquisition unit 3.

The data acquisition unit 3 contains a stationary or mobile data carrier 4, which stores the desired data for the supplier, e.g. the expected milk quantity. The desired milk charge value can be an automatically determined value of a preceding number of milk charges. If the operator establishes that the desired value differs significantly from the actual value of the milk charge, it is possible to manually give a modified desired value via the data acquisition unit 3. The data stored or inputted into the data acquisition unit 3 is now available to a control mechanism 5, in order to control the sampling means for a representative milk sample.

The sampling means 6 essentially has a peristaltic pump, which pumps from a line 11 the representative milk sample into a sample bottle 7. In addition, the pumping characteristic P can be stored in the sampling means.

The delivery of the milk charge from tank 1 to a collecting tank, such as e.g. that of a milk collecting truck or tanker, takes place in the direction of the arrow by a delivery or feed line 9, to which is connected a feed pump. The actual milk charge delivery, i.e, the start and finish of the delivery is monitored by means of sensor 8, which is at least connected to the sample means 6.

Figure 2:
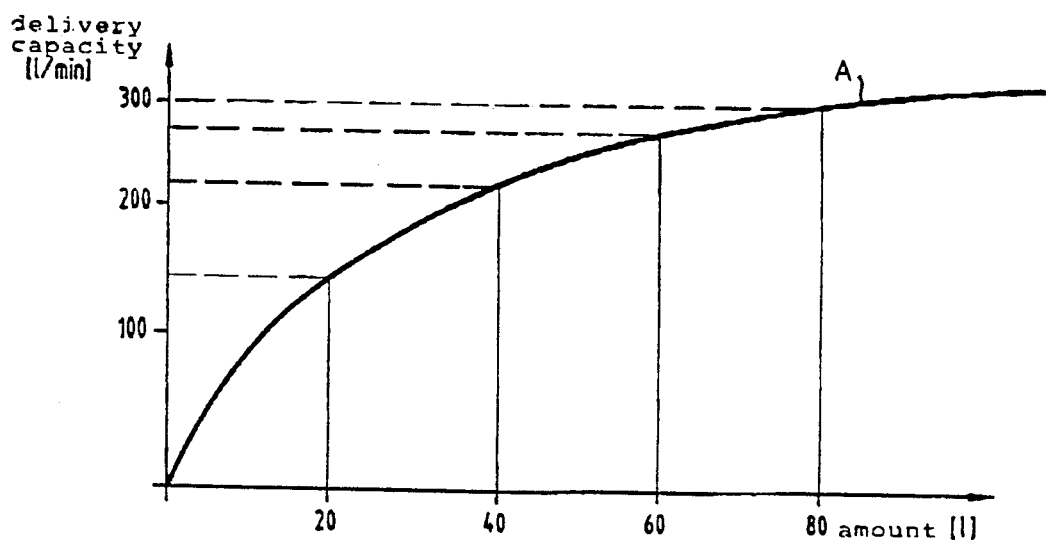
FIG. 2 is a graph showing an acceptance characteristic A with a representation of the delivery as a function of the milk charge quantity.
Figure 3:
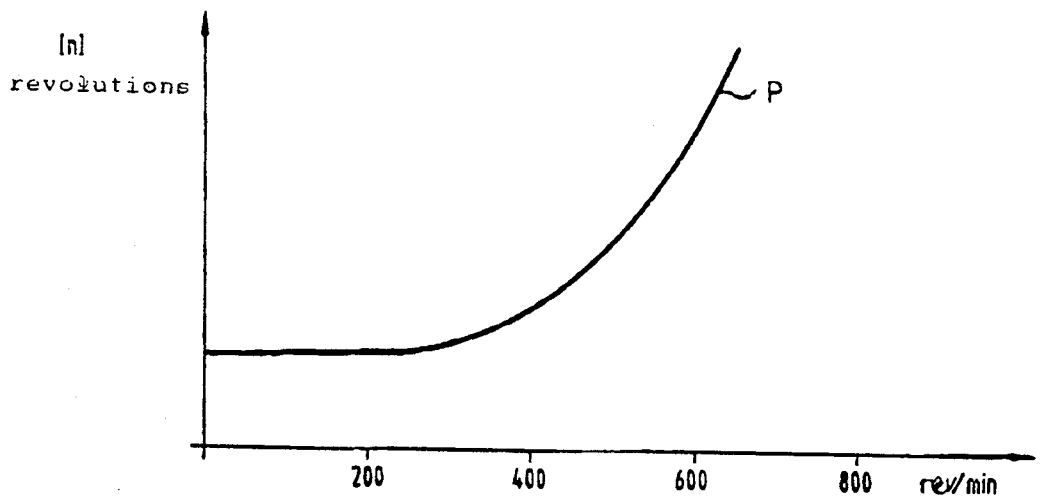
FIG. 3 is a graph showing a pumping characteristic P as a function of the number of revolutions n compared with the speed r.p.m.

On e.g. using as a basis a 50 liter milk charge, then the apparatus functions as follows. In a starting phase the feed pump for recycling the milk charge is operated for the first 20 l with a delivery of 150 l/min. This corresponds to a feed or delivery time of 8 s (seconds) (FIG. 2.) The peristaltic pump in the sampling means 6 is started at the beginning of the delivery of the milk charge by means of sensor 8 and operates with the 8 s setting corresponding to the corrected pumping characteristic P (FIG. 3).

Following this first 8 second time interval the control mechanism will transfer the next delivery corresponding to the acceptance or collecting characteristic, e.g. 230 l/min, so as to recycle the next 20 l therewith. A computer unit, which can e.g. be located in the data acquisition unit 3, correspondingly calculates a recycling time of on this occasion 5.22 s. Simultaneously for said second interval the speed of revolution of the peristaltic pump is increased and operated for a time interval of 5.22 seconds.

For the remaining 10 l of the milk charge to be recycled, the delivery is increased to 280 l/min after reaching 40 l. Correspondingly, in a third interval the feed pump and the peristaltic pump operate purely mathematically for 2.11 s.

However, the effective stopping of the peristaltic pump is controlled via sensor 8, as soon as no further milk is detected or it detects the desired value for the degree of overfilling of the sample bottle.

FIG. 2 shows an acceptance characteristic A, where the milk charge quantity to be delivered is plotted on the abscissa and the delivery in l/min on the ordinate. In the example, this acceptance characteristic A has a significant gradient and then approaches an asymptotic path for quantities of e.g. above 80 l.

The following values are given as supporting values for this acceptance characteristic: for 20 l a delivery of 150 l/min; for 40 l a delivery of 230 l/min; for 60 l approximately 280 1/min; and for 80 1 approximately 300 1/min. Acceptance characteristics of this type are generally plotted empirically and in a construction-dependent manner.

FIG. 3 shows a possible empirical pumping characteristic path. The pumping characteristic P gives the number of revolutions n (ordinate) compared with the speed r.p.m. (abscissa) for the same, pumped milk sample volume. The path of the pumping characteristic P is initially almost linear up to 200 r.p.m. and then assumes a roughly exponentially rising character.

With respect to the degree of filling and overfilling the apparatus can be programmed e.g. via the data acquisition unit in such a way that on delivering a milk charge in which the actual data correspond to the desired data, the degree of filling is defined as 100%, the effective sample bottle volume only being e.g. 75% used.

The sample bottle overfilling percentage can consequently be inputted and is normally set at 20%. It is correspondingly possible to fill the sample bottle with milk sample up to a degree of filling of 120% and in this range there are also standard variations of the milk charge volume. If, in spite of this, the milk charge delivery is to be continued and the degree of filling of the sample bottle is already 120%, then the sampling operation is stopped by the control mechanism and an error code for this milk sample is stored. The milk charge delivery obviously continues up to the end.

If there is a downward milk charge volume variation, so that the actual quantity is smaller than the desired quantity, then the aforementioned problem with regards to the degree of filling of the sample bottle does not exist. Obviously also here an "underfilling" could be looked upon as non-representative and an error report could be stored. However, as a rule the underfilling is considered to be acceptable and therefore representative for the delivered milk charge.

Thus, at the end of the delivery of the particular milk charge, the invention makes it possible to store all the values of the corresponding milk charge and the representative milk sample taken. The possibility of a printout can also be provided. In addition to the standard data such as the supplier number, date time, temperature, pH-value and volume, the sample bottle degree of filling obtained is also stored and recorded.

Thus, the invention makes it possible to largely exclude error sources of a conventional nature, so that it is possible to take representative milk sample from a corresponding milk charge.

What we claim is:

1. A process for taking a representative milk sample during delivery of a milk charge from a tank into a collecting tank by a feed pump, comprising:
   inputting supplier data and data for the milk charge into a data acquisition unit;
   supplying the inputted data to a means for controlling a sampling means;
   taking the representative milk sample using said sampling means and a peristaltic pump;
   storing delivery capacity of the feed pump as an acceptance characteristic (A) of the milk charge to be accepted;
   storing number of revolutions (n) of the peristaltic pump as a pumping characteristic (P) of the rotary velocity of the peristaltic pump for a volume (z) of the milk sample to be delivered;
   wherein the delivery capacity of the feed pump during the acceptance of the milk charge is defined by the control means as a function of the volume of the milk charge to be accepted in view of the acceptance characteristic (A); and
   wherein the number of revolutions of the peristaltic pump is controlled by the control means as a function of the rotary velocity in view of the pumping characteristic (P), and the rotary velocity of the peristaltic pump is defined as a function of the delivery capacity selected with respect to the acceptance characteristic (A).

2. A process according to claim 1, wherein delivery parameters of the milk charge takes place with stepped modifications and in particular an increase of the delivery capacity as a function of desired data and measured actual data of the milk charge.

3. A process according to claim 1, wherein desired and actual data are compared at the milk charge delivery and defined volume values for the representative milk sample can be determined at which, if exceeded, an error identification takes place.

4. A process according to claim 1, wherein the values of the degree of filling, and the degree of overfilling of a sample bottle are stored in relation to the effective volume of said bottle.

5. A process according to claim 1, wherein the expected desired volume of the milk charge to be delivered is manually inputted into the data acquisition unit.

6. A process according to claim 1, wherein the delivery capacity for milk charge delivery is controlled as a function of the acceptance characteristic and the stored values.

7. A process according to claim 1, wherein means for sensing detect the start, and finish of milk charge delivery for controlling milk sample removal.

8. A process according to claim 1, wherein the taking of the milk sample is carried out in time-controlled manner for the duration of the delivery of the milk charge.

9. A process according to claim 1, wherein the desired delivery capacity for the milk charge delivery is taken into account when setting the feed time for the milk charge in accordance with the acceptance characteristic.

10. A process according to claim 1, wherein in each case a substantially constant volume of the milk sample is taken at different milk charge quantities.

11. A process according to claim 1, wherein the degree of filling of the sample bottle for the representative milk sample to be taken takes place as a function of the actual milk delivery quantity.

12. A process according to claim 1, wherein the delivery capacity for milk charge delivery is controlled as a function of the acceptance characteristic.

13. A process according to claim 1, wherein the delivery capacity for milk charge delivery is controlled as a function of the stored values.

* * * * *